United States Patent
Chhabra et al.

(10) Patent No.: US 7,611,834 B2
(45) Date of Patent: Nov. 3, 2009

(54) METHODS AND DEVICES FOR PROTEIN ASSAYS

(75) Inventors: Swapnil Chhabra, San Jose, CA (US); José M. Cintrón, Indianapolis, IN (US); Renée Shediac, Oakland, CA (US)

(73) Assignee: Sandia Corporation, Livermore, CA (US)

( * ) Notice: Subject to any disclaimer, the term of this patent is extended or adjusted under 35 U.S.C. 154(b) by 426 days.

(21) Appl. No.: 11/239,387

(22) Filed: Sep. 30, 2005

(65) Prior Publication Data

US 2007/0231925 A1 Oct. 4, 2007

(51) Int. Cl.
*C12Q 1/00* (2006.01)

(52) U.S. Cl. .......................................................... 435/4

(58) Field of Classification Search ................. 436/514, 436/518

See application file for complete search history.

(56) References Cited

U.S. PATENT DOCUMENTS

| 4,376,110 | A | * | 3/1983 | David et al. | 435/5 |
| 5,185,266 | A | * | 2/1993 | Boyd et al. | 436/89 |
| 6,613,525 | B2 | * | 9/2003 | Nelson et al. | 435/6 |
| 6,846,638 | B2 | * | 1/2005 | Shipwash | 435/7.1 |

* cited by examiner

*Primary Examiner*—Ann Y Lam
(74) *Attorney, Agent, or Firm*—Suzannah K. Sundby, Esq.; Smith, Gambrell & Russell, LLP

(57) ABSTRACT

Methods and devices for protein assays based on Edman degradation in microfluidic channels are disclosed herein. As disclosed, the cleaved amino acid residues may be immobilized in an array format and identified by detectable labels, such as antibodies, which specifically bind given amino acid residues. Alternatively, the antibodies are immobilized in an array format and the cleaved amino acids are labeled identified by being bound by the antibodies in the array.

12 Claims, 7 Drawing Sheets

Figure 3A

The sequence as shown above is: GLDQNWKHMC (SEQ ID NO:3)

The partially characterized sequence is GXDQXWXHMC (SEQ ID NO:1)

Figure 3F

The sequence as shown above is GLDQNWKHMC (SEQ ID NO:3)

|   | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|----|----|----|----|----|----|----|----|----|----|----|
| A |   |   |   |   |   |   |   |   |   |    |    |    |    |    |    |    |    |    |    |    |
| C |   |   |   |   |   |   |   |   |   | X  |    |    |    |    |    |    |    |    |    |    |
| D |   |   | X |   |   |   |   |   |   |    |    |    |    |    |    |    |    |    |    |    |
| E |   |   |   |   |   |   |   |   |   |    |    |    |    |    |    |    |    |    |    |    |
| F |   |   |   |   |   |   |   |   |   |    |    |    |    |    |    |    |    |    |    |    |
| G | X |   |   |   |   |   |   |   |   |    |    |    |    |    |    |    |    |    |    |    |
| H |   |   |   |   |   |   |   | X |   |    |    |    |    |    |    |    |    |    |    |    |
| I |   |   |   |   |   |   |   |   |   |    |    |    |    |    |    |    |    |    |    |    |
| K |   |   |   |   |   |   | X |   |   |    |    |    |    |    |    |    |    |    |    |    |
| L |   | X |   |   |   |   |   |   |   |    |    |    |    |    |    |    |    |    |    |    |
| M |   |   |   |   |   |   |   |   | X |    |    |    |    |    |    |    |    |    |    |    |
| N |   |   |   |   | X |   |   |   |   |    |    |    |    |    |    |    |    |    |    |    |
| P |   |   |   |   |   |   |   |   |   |    |    |    |    |    |    |    |    |    |    |    |
| Q |   |   |   | X |   |   |   |   |   |    |    |    |    |    |    |    |    |    |    |    |
| R |   |   |   |   |   |   |   |   |   |    |    |    |    |    |    |    |    |    |    |    |
| S |   |   |   |   |   |   |   |   |   |    |    |    |    |    |    |    |    |    |    |    |
| T |   |   |   |   |   |   |   |   |   |    |    |    |    |    |    |    |    |    |    |    |
| V |   |   |   |   |   |   |   |   |   |    |    |    |    |    |    |    |    |    |    |    |
| W |   |   |   |   |   | X |   |   |   |    |    |    |    |    |    |    |    |    |    |    |
| Y |   |   |   |   |   |   |   |   |   |    |    |    |    |    |    |    |    |    |    |    |

The sequence as shown above is: GLDQNWKHMC (SEQ ID NO:3)

Figure 8

METHODS AND DEVICES FOR PROTEIN ASSAYS

ACKNOWLEDGMENT OF GOVERNMENT SUPPORT

This invention was made by employees of Sandia National Laboratories. The government has rights in the invention.

BACKGROUND OF THE INVENTION

1. Field of the Invention

The present invention relates to methods and devices for assaying proteins in a microfluidic environment.

2. Description of the Related Art

Prior art methods for assaying proteins are generally based on two-dimensional electrophoresis (2DE) and Edman degradation. Unfortunately, current 2DE methods allow only the most abundant proteins to be identified. Thus, most of the proteins identified by 2DE methods represent structural proteins or housekeeping proteins. See e.g. Gygi et al. (2000) PNAS USA 97:9390-9395; Gygi et al. (1999) Electrophoresis 20:310-319; Shevchenko (1996) PNAS USA 93:14440-14445; Boucherie (1996) Electrophoresis 17(11):1683-1699; Ducret (1998) Protein Science 7:706-719; and Garrels (1994) Electrophoresis 15:1466-1486. Thus, 2DE prior art methods are unsuitable for assaying proteins in micro or trace amounts.

The lack of sensitivity of current 2DE-based technology is caused primarily by a lack of separating or resolving power because high abundance proteins mask the identification of low abundance proteins. Loading more protein on the gels does not improve the situation because the Gaussian tails of the high abundance spots contaminate the low abundance proteins. The use of zoom gels (2D gels that focus on a narrow pH range) allows for minimal gains but are considered too cumbersome to be of any practical utility. See Corthals (2000) Electrophoresis 21:1104-1115. Selective enrichment methods also can be used but generally at the expense of obtaining a comprehensive view of cellular protein expression. The sensitivity of detection on 2DE gels also is problematic, because the amount of protein required for identification by mass spectrometry (MS) is near the detection limits of the most sensitive methods for visualization of the protein spots on the 2DE gels. Further, the polyacrylamide matrix typically used in 2DE gives rise to a significant amount of background in the extracted sample mixture making subsequent analysis by MS difficult. See Kinter (2000) In Protein Sequencing and Identification Using Tandem Mass Spectrometry, Wiley, N.Y. Additionally, conventional peptide extractions following in-gel digestion procedures result in substantial protein losses which are significantly detrimental to low abundance proteins. See Timperman (2000) Anal. Chem. 72:4115-4121.

Multi-dimensional column separations offer advantages over 2DE, including a higher separating power and reduced sample contamination and loss. A typical large format 2DE gel is capable of achieving a peak capacity of about 2,000 while 2D column separations can achieve peak capacities of over 20,000 for protein separations. Additionally, the stationary phases of these columns are very stable and non-reactive compared to polyacrylamide gels, leading to reduced sample contamination and loss. Many different types of separation techniques have been coupled to 2D column separations including size exclusion, reversed phase chromatography, cation-exchange chromatography, and capillary electrophoresis. See Wall (2000) Analytical Chemistry 72:1099-1111; Link (1999) Nature Biotechnology 17:676-682; Opiteck (1998) Journal of Microcolumn Separations 10:365-375; Hooker et al. (1998) In High-Performance Capillary Electrophoresis, John Wiley & Sons Inc, New York, Vol. 146, pp 581-612; Opiteck et al. (1998) Analytical Biochemistry 258:349-361; Vissers (1999) Journal of Microcolumn Separations 11:277-286; and Liu et al. (1996) Anal. Chem. 68:3928-3933. Unfortunately, multi-dimensional column separations are impractical for use in or in conjunction with microfluidic applications and devices.

Edman degradation allows protein sequencing and involves the cyclic removal and identification of the terminal amino acid based on a labeling reaction between the terminal amino group and phenylisothiocyanate (PITC). When the labeled protein is treated with acid, the N-terminal amino acid residue is cleaved as an unstable intermediate that undergoes rearrangement to a phenylthiohydantoin. The cleaved product can be identified by comparison with phenylthiohydantoin preparations of standard amino acids. The sequence of the protein or polypeptide is elucidated by cycling the protein through many stages of removal and sequential identification of the terminal amino acid residue. Alternative Edman degradation reactions employ PITC analogues and cleavage and identification of C-terminal residues.

Recently, devices for Edman degradation reactions have been miniaturized. See Wurzel & Brigitte (2000) Proteomics in Functional Genomics 88:145-157; Wurzel & Brigitte (1998) Springer, Berlin, Germany:219-224; Wurzel & Brigitte (1998) J. Protein Chem. 17(6):561-564; and U.S. Patent Application Publication No. 20040175822. Unfortunately, these devices are unsuitable for coupling or multiplexing with devices and methods for microfluidic separations and they do not allow the identification of the protein sequence directly from the microfluidic device.

Thus, a need still exists for a devices and methods for assaying and sequencing micro quantities of proteins.

SUMMARY OF THE INVENTION

The present invention provides methods and devices for protein assays based on Edman degradation in microfluidic environments.

In some embodiments, the present invention provides an assay which comprises subjecting a protein to consecutive coupling and cleaving steps to result in a plurality of cleaved amino acid residues in a microfluidic device, contacting each cleaved amino acid residue with a plurality of detectable labels, which each detectable label specifically binds a given amino acid, identifying each cleaved amino acid residue by the detectable label bound thereto, and identifying the location of each cleaved amino acid residue in the sequence of the protein. In some embodiments, each detectable label is conjugated with an antibody that specifically binds to a given amino acid residue. In some embodiments, the cleaved amino acid residues are immobilized in a microchannel in an array based on its time of cleavage in the consecutive coupling and cleaving steps. In some embodiments, the detectable labels are immobilized in an array in parallel microchannels, preferably at least 19 parallel microchannels. In some embodiments, the plurality of detectable labels are distinguishable labels which are contacted with the cleaved amino acid residues at substantially the same time in one step and then each cleaved amino acid residue and its location are identified. In some embodiments, each detectable label is sequentially contacted with the cleaved amino acid residues and the cleaved amino acid residues and their locations are identified by deduction after contact with each detectable label. In some embodiments, each detectable label is contacted with the plurality of cleaved amino acid residues in one parallel microchannel and then each amino acid residue and its location are identified. In some embodiments, each cleaved amino acid residue is contacted with the plurality of detectable labels in one parallel microchannel and then each amino acid residue and its location are identified. In some embodiments, the cleaved amino acid residues and their locations are identified by sequentially detecting each cleaved amino acid by chromatography.

In some embodiments, the present invention provides devices for conducting the methods described herein.

DESCRIPTION OF THE DRAWINGS

This invention is further understood by reference to the drawings wherein:

FIG. 2A shows a coupling reaction at a pH of about 9.0.

FIG. 2B shows the cleavage step with TFA to give an amino acid residue immobilized to PITC and the remainder of the cleaved protein free in solution.

FIG. 2C shows the beginning of the Edman degradation reaction to be repeated in the next reaction region.

FIG. 3A schematically shows 20 parallel microchannels (columns). Each microchannel comprises reaction regions containing the same immobilized cleaved amino acid residue in a given row. Arrows indicate entrances and direction of fluid flow.

FIG. 3B shows the detectable label, e.g. antibody, which was contacted with each cleaved amino acid residue immobilized in the reaction regions of a given microchannel. "X" indicates that the given detectable label specifically bound to the cleaved amino acid immobilized in the given reaction region.

FIG. 3C shows parallel microchannels with a control. Arrows indicate entrances and direction of fluid flow. "X" indicates that the given detectable label specifically bound to the cleaved amino acid immobilized in the given reaction region.

FIG. 3D shows a false negative result. Arrows indicate entrances and direction of fluid flow. "X" indicates that the given detectable label specifically bound to the cleaved amino acid immobilized in the given reaction region.

FIG. 3E shows a false positive result. Arrows indicate entrances and direction of fluid flow. "X" indicates that the given detectable label specifically bound to the cleaved amino acid immobilized in the given reaction region.

FIG. 3F schematically shows how a protein sequence may be partially characterized according to the methods and devices of the present invention. Arrows indicate entrances and direction of fluid flow. "X" indicates that the given detectable label specifically bound to the cleaved amino acid immobilized in the given reaction region.

FIG. 8 schematically shows the parallel microchannels of FIG. 7 and the how the protein sequence is characterized. Arrows indicate entrances and direction of fluid flow. "X" indicates that the given detectable label specifically bound to the cleaved amino acid immobilized in the given reaction region.

Figure 1:
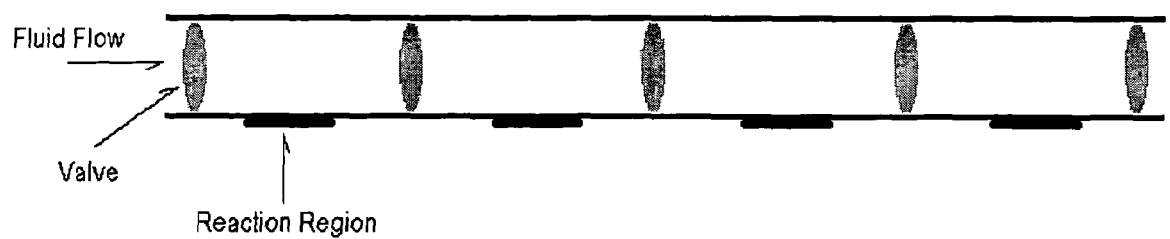
FIG. 1 schematically shows a microchannel comprising the reaction regions for Edman degradation reactions according to the present invention.

While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and sprit of the principles of the present invention.

DETAILED DESCRIPTION

The present invention provides methods and devices for assaying and sequencing proteins, preferably in micro- to nano-scale amounts, volumes, or concentrations, using Edman degradation in microchannels. The devices of the present invention are portable and do not require mass spectrometers for protein analysis. The devices of the present invention may be used as standalone devices or as modular add-on devices that may be coupled or multiplexed with other devices.

As used herein, "assaying" is used interchangeably with "detecting", "measuring", "monitoring" and "analyzing". As used herein, "protein" is used interchangeably with "peptide" and "polypeptide" and refers to two or more amino acids linked together. As used herein, "microscale" and "nanoscale" refer to concentrations of proteins ranging from about $10^{-6}$ to $10^{-9}$ M. It should be noted, however, that the methods and devices of the present invention may be used to assay and sequence proteins in amounts, volumes, or concentrations, outside of these ranges. As used herein, "affixed", "attached", "associated", "conjugated", "connected", "coupled", "immobilized", "adsorbed", and "linked" are used interchangeably and encompass direct as well as indirect connection, attachment, linkage, or conjugation, which may be reversible or irreversible, unless the context clearly dictates otherwise.

As used herein, "channel" refers to a structure wherein a fluid may flow. A channel may be a capillary, a conduit, a strip of hydrophilic pattern on an otherwise hydrophobic surface wherein aqueous fluids are confined, and the like. As used herein, "microfluidic" refers to a system or device having one or more fluidic channels, conduits or chambers that are generally fabricated at the millimeter to nanometer scale. Thus, the "microfluidic channels" or alternatively referred to herein as "microchannels" of the present invention generally have cross-sectional dimensions ranging from about 10 nm to about 1 mm.

Edman degradation reactions generally comprise two steps, a coupling step and a cleaving step, which are repeated. Each cycle of Edman degradation steps results in a cleaved amino acid residue and the remaining protein one of which is immobilized on a substrate where the other is unbound in solution. Either the N-terminal or the C-terminal amino acid residue of the protein may be cleaved and the coupling and cleaving agents used are selected based on the desired terminal amino acid residue is to be coupled or cleaved. One of ordinary skill in the art may readily select the coupling and cleaving agents.

Suitable coupling agents include phenylisothiocyanate (PITC), 7-N,N-dimethylaminosulfonyl-4-(2,1,3-benzoxadiazolyl)isothiocy-anate (DBD-NCS); 7-((N,N-dimethylamino)sulfonyl)-2,1,3-benzoxadiazol-4-yl isothiocyanate (DBD-NCS); 7-((N,N-dimethylamino)sulfonyl)-2,1,3-benzooxad-iazol-4-yl Isothiocyanate;

fluorinated isothiocyanate; fluorescein isothiocyanate (FITC); 4-(N-1-dimethylaminonaphthalene-5-sulfonylamino)phenyl isothiocyanate (DNSAPITC); 4-N,N-dimethylaminoazobenzene 4'-isothicyanate phenyllisothiocyanate (DABITC); 2-(4-isothiocyanatophenoxy)-1,3,2-dioxaphosphinane 2-oxide (PEPITC); 3-(4'(ethylene-N,N,N-trimethylamino)phenyl)-2-isothiocyanate (P(ETAP)TH); paraphenylazpphenylisothiocyanate (PAPITC); dansylamino PITC, and the like.

Suitable cleaving agents include trifluoroacetic acid (TFA), hydrofluoric acid (HF), trifluoromethanesulfonic (TFMSA), and the like.

FIG. 1 shows a cross-sectional view of a device of the present invention comprising microchannels having multiple "wells" or reaction regions. As used herein, "wells" and "reaction regions" are used interchangeably and refer to areas where Edman degradation coupling and cleavage steps may occur. The reaction regions may be of any suitable shape or size including depressions in the microchannel walls or areas substantially flush with the microchannel surfaces. In some embodiments, each reaction region comprises a valve which may be closed to prevent or inhibit reactants, products, or reagents of one coupling and cleavage cycle in a given reaction region from contaminating another reaction region. As used herein, "valve" refers to any structure or means known in the art which may be used to reversibly prevent or inhibit a fluid from flowing from one area to another area.

As used herein, "microchannel" and "channel" are used interchangeably and refer to cavities of any desired shape or configuration through which a fluid may be directed. The microchannels may allow continuous flow-through of the fluid, the microchannels may contain the fluid or a discrete amount thereof for a given amount of time, or both. For example, a microchannel may comprise a reaction region to which a fluid containing an analyte, such as a protein, flows and is then subjected to a reaction, such as Edman degradation, after which the resulting fluid and protein continue to flow through the microchannel. The microchannels may further comprise microstructures or nanostructures such as valves, membranes, filters, pumps, heaters, electrodes, beads, gels, polymers, posts, ridges, grooves, and the like for mixing, concentrating, separating, analyzing, controlling fluid flow, and the like.

As used herein, a "fluid" refers to a continuous amorphous substance that tends to flow and to conform to the outline of a container, such as a liquid or a gas. If one desires to assay a protein on or in a solid according to the present invention, the solid may be made into a fluid containing the protein using methods known in the art. For example, a solid may be dissolved in an aqueous solution, ground up or liquefied, dispersed in a liquid medium, and the like. Alternatively, the surface of the solid may be tested by washing the surface with a solution such as water or a buffer and then assaying the protein, if any, in the solution.

The devices of the present invention are preferably made of materials that are suitable for micromachining or microfabrication, such as silicon, silica, quartz, glass, controlled pore glass, carbon, alumina, titania, tantalum oxide, germanium, silicon nitride, zeolites, gallium arsenide, gold, platinum, aluminum, copper and titanium, polymers, combinations thereof, and the like. In some embodiments, the devices are preferably made of materials that are optically transparent. In some embodiments, the devices are preferably made of materials that do not substantially affect the assay and reagents in which the devices are employed. In preferred embodiments, the substrates comprise polymers such as polystyrene; poly (tetra)fluoroethylene (PTFE); polyvinylidenedifluoride; polycarbonate (PC); polymethylmethacrylate (PMMA); polyvinylethylene; polyethyleneimine; poly(etherether)ketone; polyoxymethylene (POM); polyvinylphenol; polylactides; polymethacrylimide (PMI); polyetherimide (PEI), cyclo-olefin, polyalkenesulfone (PAS); polypropylene; polyethylene; polyhydroxyethylmethacrylate (HEMA); polydimethylsiloxane (PDMS); polyacrylamide; polyimide; and block-copolymers, and the like, and combinations thereof.

In some embodiments of the present invention, a coupling agent is immobilized in the reaction regions directly or indirectly by immobilizing onto beads, films, porous polymer monoliths, and the like that are then immobilized in the reaction regions using methods known in the art, including noncontact ink jet technology, photolithography, microcontact printing, nanografting, and spot arraying. See e.g. U.S. Patent Applications: 20030068446, 20020084429, 20020123227, 20030059537, 20030153010, 20040053354, 20040213910, and the like; U.S. Pat. Nos. 6,776,094, 6,579,673, 6,579,463, 6,541,022, 6,518,194, 6,444,254, 6,180,239, 5,965,305, 5,847,019, 5,773,308, 5,622,826, and the like; Publications and books: INTRODUCTION TO BIOPHOTONICS by Paras N. Prasad Wiley-Interscience (2003), PROTEIN MICROARRAY TECHNOLOGY by Dev Kambhampati (Editor) John Wiley & Sons (2004), BIOCONJUGATION PROTOCOLS: STRATEGIES AND METHODS (Methods in Molecular Biology (Clifton, N.J.), V. 283) by Christof M. Niemeyer, John M. Walker Humana Press; (2004), DNA MICROARRAYS AND GENE EXPRESSION: FROM EXPERIMENTS TO DATA ANALYSIS AND MODELING by Pierre Baldi, G. Wesley Hatfield, Wesley G. Hatfield Cambridge University Press (2002), NANOBIOTECHNOLOGY: CONCEPTS, APPLICATIONS AND PERSPECTIVES by Christof M. Niemeyer (Editor), Chad A. Mirkin (Editor) John Wiley & Sons (2004), and Blaws & Reichert (1998) *Protein Patterning*, Biomaterials 19:595-609, PROTEIN MICROARRAYS by M. Schena (Editor) Jones and Bartlett (2005) and the like, all of which are herein incorporated by reference.

Since Edman degradation requires relatively harsh pH conditions, to prevent leaching of the coupling agent, composite materials comprising the coupling agent covalently bound to a material such as glass, fused silica, quartz, gold, Teflon® and the like. These composite materials may be formed into any desired shape including beads, films, porous monoliths, and the like. The composite materials may be formed via a one step (base or acid catalyzed) sol-gel process or other methods known in the art. See Buchel et al. (1998) Supramolec. Sci. 5:253; Reynolds & Colón (2000) J. Liq. Chromatogr Relat. Tech. 21:161-173; Rodriguez & Colón (2001) Appl. Spectrosc. 55:472-480; Cintrón & Colón (2002) Analyst 127:701-704; Guo & Colón (1996) Chromatographia 43:477-483; Guo & Colón (1995) J. Microcol. September 7:485-491; and Guo & Colón (1995) Anal. Chem. 67:2511-2516; and U.S. Pat. No. 5,869,152, which are herein incorporated by reference. In some embodiments, the sides or surfaces defining the reaction regions are made of a composite material comprising the covalently bound coupling agents.

In some embodiments, more than one coupling agent is used. For example, PITC and at least one other coupling agent known in the art may be used. In some embodiments, the coupling agent may be immobilized in the microchannels in a desired array format. As used herein, "array" refers to one or more objects including microchannels and compounds that are spatially arranged with respect to each other. Once the coupling agents are immobilized in the reaction regions, the Edman degradation cycles are sequentially conducted to provide immobilized amino acid residues in consecutive reaction regions.

In some embodiments, the physical area of an array to that will have an agent or object immobilized thereon may be readily modified and optimized by one skilled in the art. For example, the areas may be subjected to reactive ion etching such that a given compound, protein or antibody will readily adhere thereto. See U.S. patent application Ser. No. 11/022,862, and Rucker et al., (2005), Langmuir 21:7621-7625, which are herein incorporated by reference.

Figure 2A:
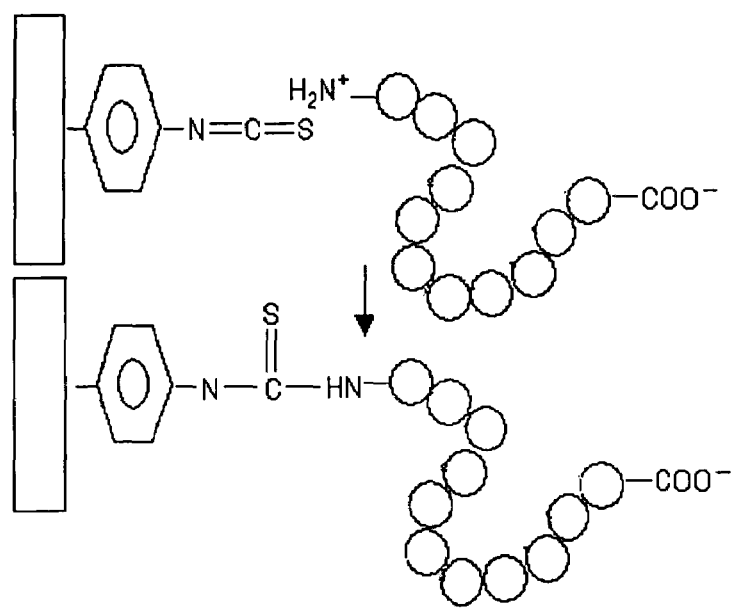
FIGS. 2A-2C schematically show two consecutive Edman degradation reactions of the present invention using PITC immobilized in reaction regions in a microfluidic device. As shown in the figures, PITC is immobilized on a substrate.
Figure 2B:
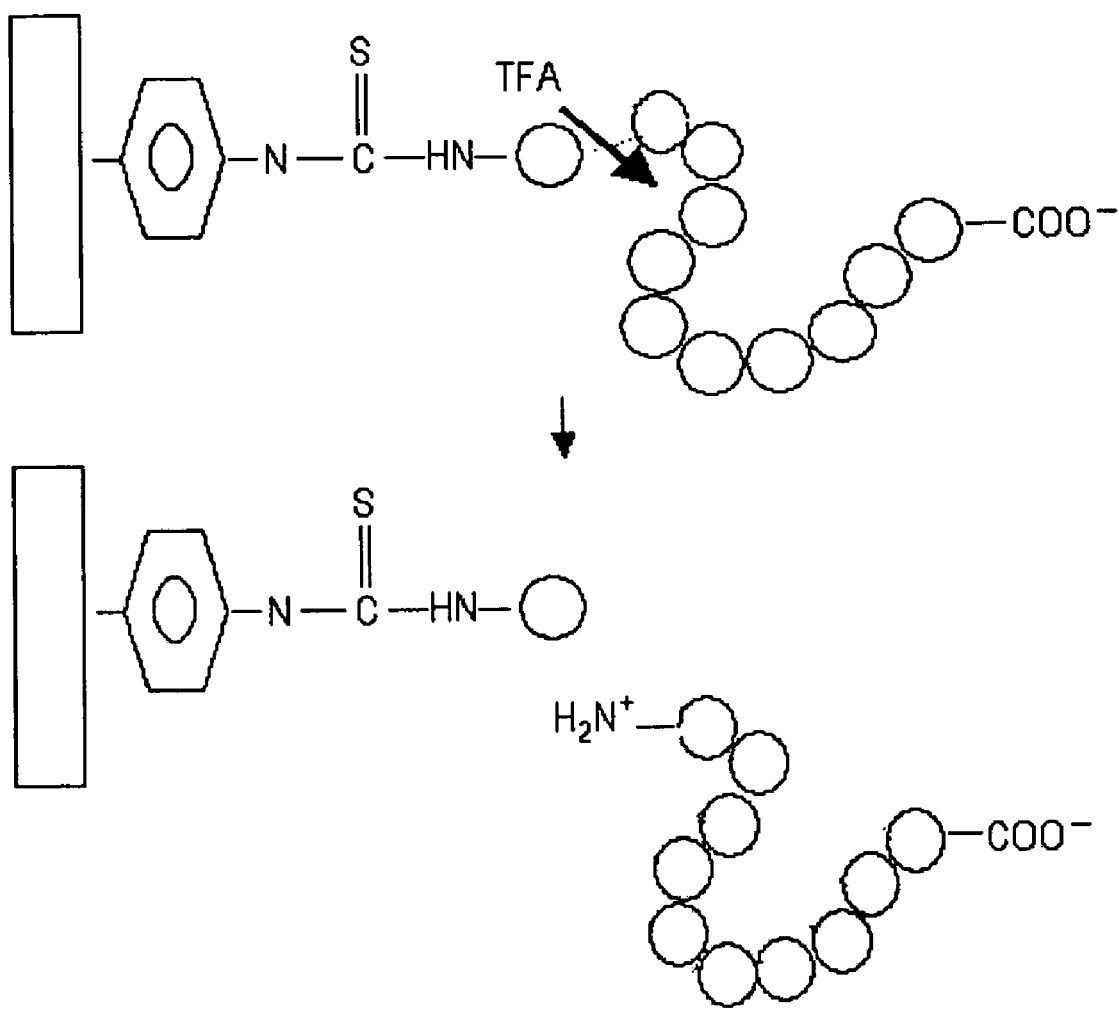
Figure 2C:
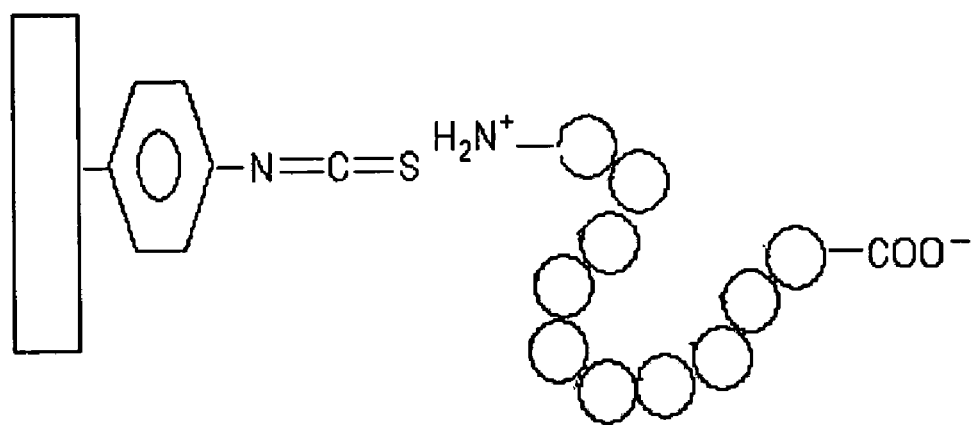

FIGS. 2A-2C illustrate reaction chemistry details on Edman degradation performed in two of the reaction regions of a device of the present invention. A given protein is placed in a reaction region then, as shown in FIG. 2A, the protein is coupled to a coupling agent, such as PITC, immobilized in the reaction region, at a pH of about 9.0. The coupling occurs between the immobilized coupling agent and a free terminus of the protein, thereby immobilizing the protein. Next, as shown in FIG. 2B, the immobilized protein is treated with a cleaving agent, such as trifluoroacetic acid (TFA), to selectively cleave the terminal amino acid bond. The cleaving step results in a cleaved amino acid residue coupled with the immobilized coupling agent and the remaining protein unbound. As shown in FIG. 2C, the unbound protein is moved to the next reaction region where the protein is subjected to the coupling and cleaving steps. The steps of moving the protein to the reaction region and then coupling and cleaving the protein are repeated as desired. Preferably, the steps are repeated as many times as necessary to couple and cleave each amino acid residue of the protein.

In some embodiments, several Edman degradation cycles may be performed in parallel channels on a device of the present invention. In preferred embodiments, the devices comprise about twenty parallel channels as shown in FIG. 3A. In some embodiments, the devices may comprise one or more channels for controls. In some embodiments, proteins having the same amino acid sequence are subjected to Edman degradation cycles in each of the twenty parallel channels. Such parallel Edman degradation cycles result in the amino acid residues sequentially immobilized in the reaction regions. The immobilized amino acid residues may then be detected or identified, thereby allowing the sequence of the protein to be characterized using methods know in the art.

In preferred embodiments, a detectable label that specifically binds only one amino acid residue is introduced into one parallel channel, and a detectable label that specifically binds a different amino acid residue is introduced into a different parallel channel, and so on. As used herein, "detectable label" refers to a molecule capable of detection using methods known in the art including radiography, fluorescence, chemiluminescence, enzymatic activity, absorbance, and the like. Detectable labels include radioisotopes, fluorophores, chromophores, enzymes, dyes, metal ions, ligands such as biotin, avidin, streptavidin and haptens, quantum dots, and the like. As used herein, "specifically binds" refers to the specific interaction of one of at least two different molecules for the others compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

The sequence of the protein is then characterized by reading or detecting the labels across the columns. For example, as shown in FIG. 3B, a detectable label that specifically binds with alanine is contacted with the amino acid residues immobilized in the reaction regions of the first microchannel. The reaction regions in which the detectable labels that are specific for the other amino acid residues are contacted with are shown in FIG. 3B. As shown in FIG. 3B, the first immobilized amino acid residue (row 1) that exhibits a detectable label in the reaction region of channel 6. Detectable labels are marked as "X". The detectable label that was contacted with the reaction regions in channel 6 specifically binds the amino acid residue, glycine. Thus, the first amino acid residue is glycine. The next immobilized amino acid residue (row 2) that exhibits a detectable label is in channel 10. The reaction regions of channel 10 were contacted with detectable labels that were specific for leucine. This sequential identification of the immobilized amino acid residues is repeated until the sequence of the protein is characterized. It should be noted that where the N-terminus of the protein is immobilized and cleaved, that the amino acid sequence determined is in reverse, i.e. the amino acid residue in the first reaction region is the last amino acid in the protein.

In some embodiments, the last reaction region of each column comprises an immobilized control amino acid residue for which the given detectable label that will be contacted with the amino acid residues in the reaction regions of a given column specifically binds. For example, as shown in FIG. 3C, in the first column, last reaction region, the control amino acid residue is alanine. Lack of a detectable label on a control amino acid residue indicates a false negative result. As shown in FIG. 3C, there is no detectable label on the control amino acid residue in channel 2, thereby indicating the possibility of a false negative result.

In embodiments where there are only 19 detectable labels that are specific for 19 of the amino acid residues, lack of a detectable label in the same positions across all the channels may be interpreted as having the amino acid residue for which no detectable label is available. For example, as shown in FIG. 3D, there is no detectable label available for amino acid residue histidine. In these embodiments, where no other detectable labels are detected at the corresponding reaction region in the other channel, one may assume that the amino acid residue at that position is histidine. Alternatively, as shown in FIG. 3E, a detectable label which binds the amino acid residue non-specifically, contacted with the reaction regions in the given column. In this embodiment, false negative results for the given amino acid residue may be readily apparent.

In preferred embodiments, the detectable label is conjugated to an antibody that specifically binds a given amino acid residue. The antibodies may be made using methods known in the art or obtained from commercial sources and the detectable labels may be conjugated to the antibodies using methods known in the art. The binding or interaction between a given amino acid residue with the antibody that specifically binds the amino acid residue results in an antibody bound to the immobilized amino acid-PITC conjugate in each well. The bound antibodies may then be detected using methods known in the art. In preferred embodiments an antibody specific for a given amino acid does not bind or interact with other amino acid residues in detectable amounts. As used herein, an "antibody" refers to a polypeptide substantially encoded by an immunoglobulin gene or immunoglobulin genes, or fragments thereof which specifically bind and recognize a given analyte (antigen) or fragment thereof.

At present, there are 15 antibodies that specifically bind to 15 amino (out of 20) amino acids which are available commercially (Chemicon Internatinoal, Temecula, Calif.). The remaining amino acid residues without a corresponding antibodies are asparagine, leucine, lysine, proline, and threonine. Thus, as shown in FIG. 4F, the amino acid residues at position 2, 5, and 7 of the protein would be unknown and each could be one of the amino acid residues selected from asparagine, leucine, lysine, proline, and threonine.

Alternatively, one skilled in the art may readily make and use antibodies which specifically bind asparagine, leucine, lysine, proline, and threonine using methods known in the art. See e.g. Kohler & Milstein (1975) Nature 256:495-497; U.S. Pat. No. 4,376,110, Kosbor et al. (1983) Immunology Today 4:72; Cole et al. (1983) PNAS USA 80:2026-2030; Cole et al. (1985) Monoclonal Antibodies And Cancer Therapy, Alan R. Liss, Inc., pp. 77-96, which are herein incorporated by reference.

In embodiments, such as these, where detectable labels specific for two or more amino acids are not available or are lacking, the devices and methods of the present invention may still be used to identify a protein from known protein sequences. One skilled in the art may readily analyze the sequence of the partially characterized protein with one or more known or given sequences using sequence alignment methods known in the art to determine whether the partially characterized protein is one of the known or given proteins.

For example, the partially characterized protein sequence is GXDQXWXHMC (SEQ ID NO:1). The sequence of the partially characterized protein is compared to known sequence A for protein A, which is SIHGPAGDFY (SEQ ID NO:2), known sequence B for protein B, which is GLDQNWKHMC (SEQ ID NO:3), and know sequence C for protein C, which is GVDQNSKHMC (SEQ ID NO:4). Based on the little to no sequence identity with sequence A, the partially characterized protein is not protein A. Since there is 100 percent sequence identity between the identified amino acid residues of the partially characterized when compared to the corresponding positions of sequence B, the partially characterized protein can be identified as being protein B with a high degree confidence. Since there is a high percent sequence identity between the identified amino acid residues of the partially characterized when compared to the corresponding positions of sequence C, the partially characterized protein is likely an analogue of protein C or the partially characterized protein belongs to the same family of proteins as protein C.

It should be noted that where 19 or more detectable labels are distinguishable from each other, the Edman degradation cycles need only be performed in one channel. In these embodiments, the distinguishable labels may include a combination of detectable labels. As used herein, a "distinguishable label" is a detectable label that may be distinguished from another detectable label. For example, where only 4 detectable labels are available, the 4 distinguishable labels may be mixed and weighted and attached to a ligand that specifically binds a specific amino acid to produce 23 different and distinguishable labels. For example, where only 4 colors of fluorophores, blue (B), red (R), green (G), and yellow (Y), are available, they may be mixed and weighted using methods known in the art. For example, 1 part blue and 3 parts red may be attached to an antibody specific for alanine, 2 parts blue and 2 parts red can be attached to an antibody specific for lysine, 3 parts blue and 1 part red can be attached to tyrosine, etc. Each color mixture will produce a characteristic wavelength that may be distinguished from others, thereby giving 23 distinguishable labels.

Figure 4:
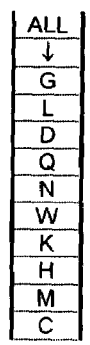
FIG. 4 shows an embodiment of the present invention where distinguishable labels may be used to identify immobilized amino acid residues in a single microchannel.

FIG. 4 shows a single microchannel where each distinguishable and detectable label was contacted with each reaction region. The single letter amino acid designations are used to show each distinguishable detectable label. The distinguishable labels which do not bind the first amino acid residue immobilized in the first reaction region are moved to the next reaction regions until binding with its given amino acid. It should be noted that in these embodiments, sufficient quantities of each distinguishable label should be used such that excess of each detectable label is washed through the channel and the excess may be observed upon exiting the channel.

Figure 5:
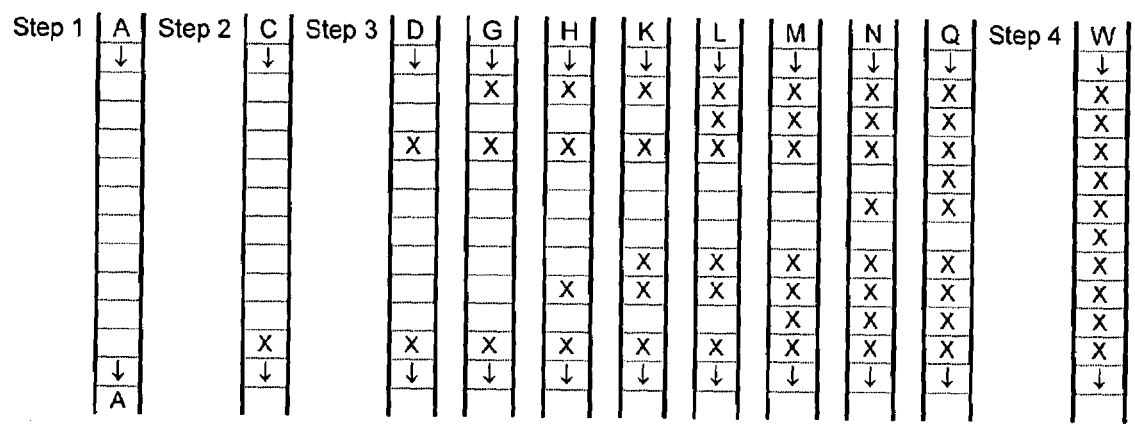
FIG. 5 is a schematic showing how a protein may be characterized by sequentially contacting detectable labels with amino acid residues immobilized in reaction regions of one microchannel. Arrows indicate entrances and direction of fluid flow. "X" indicates that the given detectable label specifically bound to the cleaved amino acid immobilized in the given reaction region. Step 1: The first detectable label is contacted with all the reaction regions in the single column. As shown, the detectable label for alanine does not bind to any amino acid residues in the reaction regions. Step 2: The next detectable label, which is specific for cysteine, is contacted with all the reaction regions in the single column. A detectable label is observed at the $10^{th}$ reaction region of the microchannel. Step 3: The next detectable label, which is specific for aspartic acid, is contacted with all the reaction regions in the single column. Detectable labels are observed at the $3^{rd}$ and $10^{th}$ reaction regions. Since the $10^{th}$ reaction region was previously determined to be another amino acid residue, cysteine is calculated to be the third amino acid residue in the protein. Step 4: The process is repeated until all reaction regions in the single microchannel exhibit detectable labels as shown.

In embodiments where the detectable labels that specifically bind given amino acid residues are indistinguishable from each other, the detectable labels may be introduced into the single channel sequentially. Prior to introducing the next detectable label, the locations of the detectable labels are determined and recorded such that the different antibodies having the same or indistinguishable detectable label which are introduced later may be calculated by discounting the previously recorded detectable labels. FIG. 5 is a schematic of this sequential process.

In some embodiments of the present invention, a protein is immobilized in the reaction regions directly in the reaction regions or indirectly by immobilizing onto beads, films, membranes, gels, porous polymer monoliths, and the like that are then immobilized in the reaction regions using methods known in the art, including non-contact ink jet technology, photolithography, microcontact printing, nanografting, and spot arraying using methods known in the art.

Figure 6:
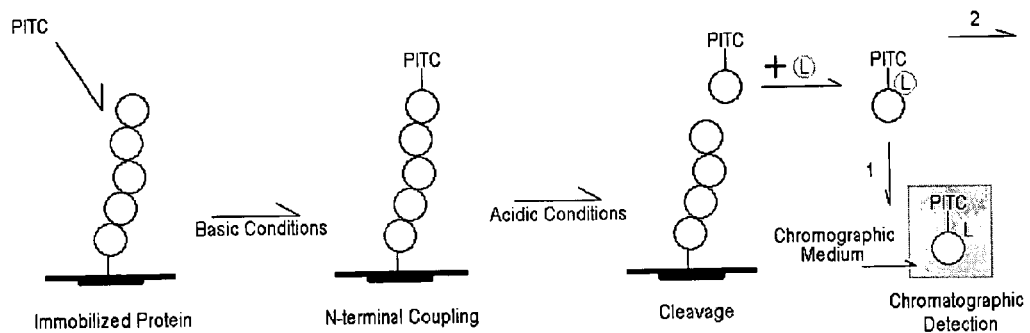
FIG. 6 shows embodiments of the present invention wherein the protein chain is immobilized and then cleaved amino acid residues are labeled and then detected by (1) chromatography, or (2) antibody-based methods.

FIG. 6 shows a reaction scheme of Edman degradation utilizing immobilized protein in reaction regions according to the present invention. The protein is coupled to an unbound coupling agent, such as PITC, at a pH of about 9.0, thereby immobilizing the coupling agent. Next, treatment with a cleaving agent, such as TFA, selectively cleaves the terminal amino acid bond. The cleaving step results in an unbound cleaved amino acid residue to which a detectable label is conjugated. In some embodiments, the unbound cleaved amino acid is moved to another region or microchannel where the detectable label is then conjugated thereto. The immobilized protein is subjected to repeated coupling and cleaving steps, and the resulting cleaved amino acids are labeled and detected sequentially.

In some embodiments, as shown in FIG. 6 at 1, the unbound labeled cleaved amino acid is detected using chromatography methods known in the art including electrochromatography (Singh (2002) Anal. Chem. 74:784-789, which is herein incorporated by reference), micellar electrokinetic chromatography, or reverse-phase high pressure liquid chromatography. In these embodiments, the unbound labeled cleaved amino acid is preferably moved to a microchannel filled with chromatographic stationary phase media such as porous polymer monoliths, micelles, beads, gels, and the like, and then identified. In some embodiments, the detectable label is a fluorophore and chromatography is coupled with fluorescence detection, wherein the amino acid is identified based on its retention time in the chromatographic stationary phase medium. The sequence of the protein is characterized by sequentially detecting cleaved amino acids after each Edman degradation cycle. The chromatographic stationary phase is washed with buffer after each amino acid is cleaved and detected. In some embodiments, the unbound labeled cleaved amino acid (at 2 of FIG. 6) is sent to micro-light sources such as diode pumped solid state lasers (Blue Sky Research, Japan), or one of several opto-electronic devices from Newport Corp (Irvine, Calif.) and Perkin Elmer Optoelectronics (Fremont, Calif.).

Figure 7:
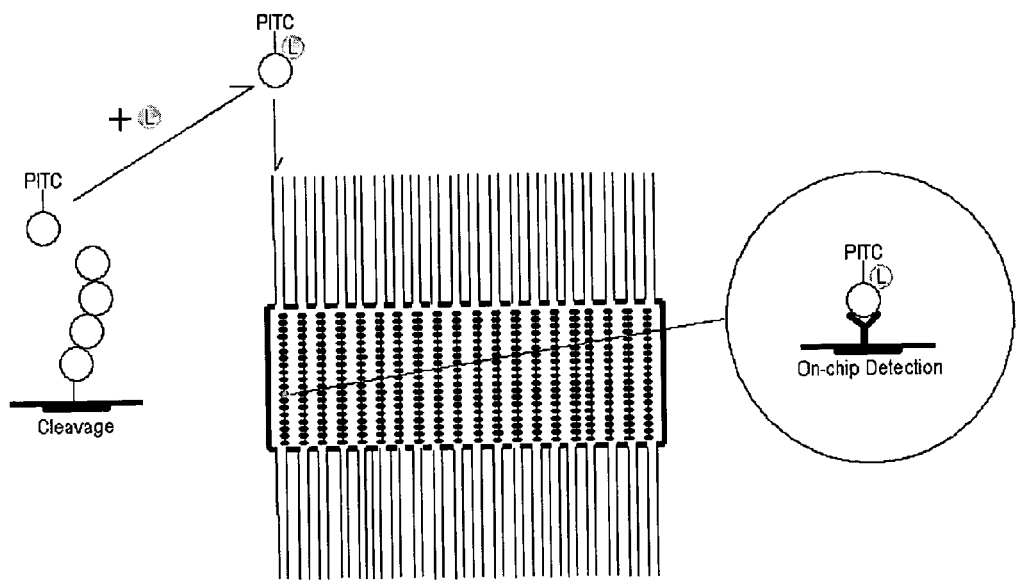
FIG. 7 schematically shows an embodiment wherein the cleaved amino acid residue is labeled and then introduced to a microchannel having 20 reaction regions each having an antibody specific for a given amino acid residue immobilized thereon. When a cleaved amino acid residue comes into contact with its respective antibody, the cleaved amino acid residue is immobilized in the given reaction region by the antibody. The identity of the amino acid residue is then determined by the specific antibody in the given reaction region.

As provided in FIG. 7, in some embodiments, the unbound labeled cleaved amino acid is moved through a microchannel having 20 reaction regions each having an antibody which specifically binds to one of the 20 amino acids immobilized therein. The antibodies are immobilized either directly or indirectly (via beads, films, membranes, gels, porous polymer monoliths, and the like) using methods known in the art. The antibodies are preferably immobilized in the microchannels in an array format as shown in FIG. 8. In some embodiments, the devices comprise about 20 parallel microchannels. After the first Edman degradation cycle, the cleaved amino acid is directed to channel 1, after the second Edman degradation cycle, the cleaved amino acid is directed to channel 2, and so forth. Each amino acid residue is identified by the particular antibody which specifically binds it. The sequence of the protein is then characterized by reading or detecting labels across the channels. For example, as shown in FIG. 8, the first cleaved amino acid residue is introduced into channel (column) 1. The reaction region having antibodies which specifically bind glycine amino acid residues, binds the first cleaved amino acid residue, thereby indicating that the first amino acid is glycine. This sequential identification of the immobilized amino acid residues is repeated until the sequence of the protein is characterized. It should be noted that where the N-terminus of the protein is immobilized and cleaved, that the amino acid sequence determined is in reverse, i.e. the amino acid residue in the first reaction region is the last amino acid in the protein.

In some embodiments, the amino acid residue bound in a reaction region, for example, the bound amino acid in FIG. 2B, is released from the reaction region using methods known in the art. The amino acid residue is then conjugated with a detectable label and detected using chromatography methods known in the art including electrochromatography, micellar electrokinetic chromatography, or reverse-phase high pressure liquid chromatography. In these embodiments, the unbound labeled cleaved amino acid is preferably moved to a microchannel filled with chromatographic stationary phase media such as porous polymer monoliths, micelles, beads, gels, and the like, and then identified. In some embodiments, the detectable label is a fluorophore and chromatography is coupled with fluorescence detection, wherein the amino acid is identified based on its retention time in the chromatographic stationary phase medium. The sequence of the protein is characterized by sequentially detecting cleaved amino acids after each Edman degradation cycle. The chromatographic stationary phase is washed with buffer after each amino acid is cleaved and detected.

Where the amino acid sequence of the protein has more residues than the number of reaction regions in a given microchannel or an array of parallel microchannels, the microchannel or array maybe operably linked with one or more additional microchannels or arrays such that undigested proteins can be moved into the reaction regions of the next microchannel or set of microchannels for further coupling and cleaving. As used herein, "operably linked" refers to two or more microchannels between which reactants, reagents, or products may readily move and be subjected to further analysis, processing, and the like.

The devices and microchannels of the present invention may comprise various geometries and architectures. In some embodiments, the microchannels are in substantially the same plane. As used herein, the term "parallel" with respect to "parallel microchannels" is not limited to its common geometric definition, but also refers to two or more microchannels having reaction regions that may be correlated to one another. For example, two microchannels may be placed at an angle to each other with their inlet ports in close proximity to each other. Each microchannel has the same number of reaction regions wherein proteins having the same sequence are subjected to consecutive Edman degradation cycles to result in the same amino acid residues immobilized in corresponding reaction regions of both microchannels. Thus, the microchannels are considered to be parallel microchannels.

In some embodiments, the devices of the present invention comprise an entrance, such as an inlet port, through which the protein to be assayed is provided. The devices may comprise structures for mixing or concentrating the protein. Suitable structures including posts, ridges, grooves, and the like, and methods known in the art may be used. See e.g. Fintschenko, et al. (2004) Anal. Chem. 76:1571-1579; and Stroock et al. (2002) Science 295:647-651, which are herein incorporated by reference. The devices may comprise chambers which comprise buffers and reagents used for assaying the protein. In some embodiments, the devices comprise structures and reagents for purifying or separating a protein to be assayed from other particles in a sample using methods known in the art including field-flow-fractionation, thin layer chromatography, affinity chromatography using immobilized capture reagents, and the like.

The methods and devices of the present invention may be used for medical applications such as assays proteins that are indicative of given diseases including antibodies, antigens, toxins, mutated proteins, and the like. The methods and devices of the present invention may be used for environmental applications such as assays for toxins and proteins indicative of given bacteria, insecticides, pesticides, herbicides, and the like, in food supplies or other environmental media, e.g., water and air. The methods and devices of the present invention may used to assay for proteins indicative of chemical and biological agents that may be used in biochemical warfare such as organisms belonging to the genera *Bacillus, Mycobacterium, Francisella, Brucella, Clostridium, Yersinia, Variola, Orthopox,* and *Burkholderia*, viruses such as those that cause Congo-Crimean hemorrhagic fever (CCHF), Ebola Haemorrhagic Fever, Rift Valley Fever (RVF), smallpox, and Venezuelan equine encephalitis (VEE), toxins such as *Clostridium* neurotoxins, ricin toxin, saxitoxin, enterotoxins, exotoxins, mycotoxins, and the like, tabun, sarin, soman, methylphosphonothioic acid, sulfur mustard, nitrogen mustard, lewisite, phosgene oximine, phosgene, diphosgene, chloropicrin, organophosphates (OPs), pesticides, insecticides, and the like. These and other application for which the methods and devices of the present invention are suitable will be readily apparent to those skilled in the art.

To the extent necessary to understand or complete the disclosure of the present invention, all publications, patents, and patent applications mentioned herein are expressly incorporated by reference therein to the same extent as though each were individually so incorporated.

Variations, modification, and other implementations of what is described herein will occur to those of skill in the art without departing from the spirit and scope of the invention and the following claims.

What is claimed is:

1. An assay comprising
   subjecting a protein to consecutive coupling and cleaving steps to result in a plurality of cleaved amino acid residues in a microfluidic device,
   contacting each cleaved amino acid residue with a plurality of antibodies, which each antibody specifically binds a given amino acid,
   identifying each cleaved amino acid residue by the antibody bound thereto, and
   identifying the location of each cleaved amino acid residue in the sequence of the protein.

2. The assay of claim 1, wherein each antibody is conjugated to a detectable label.

3. The assay of claim 1, wherein the cleaved amino acid residues are immobilized in a microchannel in an array based on its time of cleavage in the consecutive coupling and cleaving steps.

4. The assay of claim 1, wherein the antibodies are immobilized in an array in parallel microchannels.

5. The assay of claim 3, which further comprises obtaining at least 19 parallel microchannels.

6. The assay of claim 3, wherein the each antibody is conjugated to a distinguishable label and the antibodies are contacted with the cleaved amino acid residues at substantially the same time in one step and then each cleaved amino acid residue and its location are identified.

7. The assay of claim 3, wherein each antibody is sequentially contacted with the cleaved amino acid residues and the cleaved amino acid residues and their locations are identified by deduction after contact with each antibody.

8. The assay of claim 5, wherein each antibody is contacted with the plurality of cleaved amino acid residues in one parallel microchannel and then each amino acid residue and its location are identified.

9. The assay of claim 4, wherein each cleaved amino acid residue is contacted with the plurality of antibodies in one parallel microchannel and then each amino acid residue and its location are identified.

10. The assay of claim 1, wherein the cleaved amino acid residues and their locations are identified by sequentially detecting each cleaved amino acid by chromatography.

11. A microfluidic device comprising
    at least one microchannel having an amino acid residue bound to an antibody that specifically binds the amino acid residue and said antibody is conjugated to a detectable label.

12. The microfluidic device of claim 11, and further comprising one or more parallel microchannels.

\* \* \* \* \*

```
                              SEQUENCE LISTING

<160> NUMBER OF SEQ ID NOS: 4

<210> SEQ ID NO 1
<211> LENGTH: 10
<212> TYPE: PRT
<213> ORGANISM: Artificial
<220> FEATURE:
<223> OTHER INFORMATION: No known organism, i.e. synthetic, exemplary
      sequence not important for determining patentability.
<220> FEATURE:
<221> NAME/KEY: misc_feature
<222> LOCATION: (2)..(2)
<223> OTHER INFORMATION: Xaa is any amino acid residue.
<220> FEATURE:
<221> NAME/KEY: misc_feature
<222> LOCATION: (5)..(5)
<223> OTHER INFORMATION: Xaa is any amino acid residue.
<220> FEATURE:
<221> NAME/KEY: misc_feature
<222> LOCATION: (7)..(7)
<223> OTHER INFORMATION: Xaa is any amino acid residue.

<400> SEQUENCE: 1

Gly Xaa Asp Gln Xaa Trp Xaa His Met Cys
1               5                   10

<210> SEQ ID NO 2
<211> LENGTH: 10
<212> TYPE: PRT
<213> ORGANISM: Artificial
<220> FEATURE:
<223> OTHER INFORMATION: No known organism, i.e. synthetic, exemplary
      sequence not important for determining patentability.

<400> SEQUENCE: 2

Ser Ile His Gly Pro Ala Gly Asp Phe Tyr
1               5                   10

<210> SEQ ID NO 3
<211> LENGTH: 10
<212> TYPE: PRT
<213> ORGANISM: Artificial
<220> FEATURE:
<223> OTHER INFORMATION: No known organism, i.e. synthetic, exemplary
      sequence not important for determining patentability.

<400> SEQUENCE: 3

Gly Leu Asp Gln Asn Trp Lys His Met Cys
1               5                   10

<210> SEQ ID NO 4
<211> LENGTH: 10
<212> TYPE: PRT
<213> ORGANISM: Artificial
<220> FEATURE:
<223> OTHER INFORMATION: No known organism, i.e. synthetic, exemplary
      sequence not important for determining patentability.

<400> SEQUENCE: 4

Gly Val Asp Gln Asn Ser Lys His Met Cys
1               5                   10
```